United States Patent [19]

Malczewski

[11] Patent Number: 5,265,031
[45] Date of Patent: Nov. 23, 1993

[54] DIAGNOSTIC GAS MONITORING PROCESS UTILIZING AN EXPERT SYSTEM

[75] Inventor: Mark L. Malczewski, North Tonawanda, N.Y.

[73] Assignee: Praxair Technology, Inc., Danbury, Conn.

[21] Appl. No.: 618,115

[22] Filed: Nov. 26, 1990

[51] Int. Cl.⁵ .................... G01N 21/00; G06F 15/46
[52] U.S. Cl. ................................ 364/497; 395/911
[58] Field of Search ......... 364/497, 498, 499, 551.01, 364/413.02, 413.01; 395/50, 52, 904, 906, 911, 914, 902

[56] References Cited

U.S. PATENT DOCUMENTS

| | | | |
|---|---|---|---|
| 4,591,983 | 5/1986 | Bennett et al. | 395/65 |
| 4,642,782 | 2/1987 | Kemper et al. | 395/62 |
| 4,648,044 | 3/1987 | Hardy et al. | 395/76 |
| 4,658,370 | 4/1987 | Erman et al. | 395/76 |
| 4,670,848 | 6/1987 | Schramm | 395/60 |
| 4,713,775 | 12/1987 | Scott et al. | 395/50 |
| 4,891,186 | 1/1990 | Roberge | 422/83 |
| 5,039,409 | 8/1991 | Biaffert et al. | 364/497 |

OTHER PUBLICATIONS

Miller et al; "A Case Study in the Use of an Advanced Expert System Tool for Diagnosis of Cardiovascular Disease"; Journal of Clinical Engineering; vol. 11, No. 6, Nov.-Dec., 1986, pp. 449-452.

*Primary Examiner*—Thomas G. Black
*Assistant Examiner*—Mike Zanelli
*Attorney, Agent, or Firm*—E. Lieberstein

[57] ABSTRACT

A process for the continuous analysis of trace contaminants in a process gas of $O_2$, N, Ar or $H_2$. A sample of the process gas is passed through a plurality of analyzers with each dedicated to detect the presence of a predetermined trace contaminant and to provide an output signal corresponding to the level of trace impurity detected. A status signal is generated representative of preselected parameters of analyzer operation. The output and status signals are converted by a computer into data values. A rule based program provides a problem analysis to identify distinct problems based on the examination of the data values. The rule based program is executed by a separate command program which matches the problems identified by the rule based program with remedial actions to remedy erroneous conditions of analysis.

10 Claims, 10 Drawing Sheets

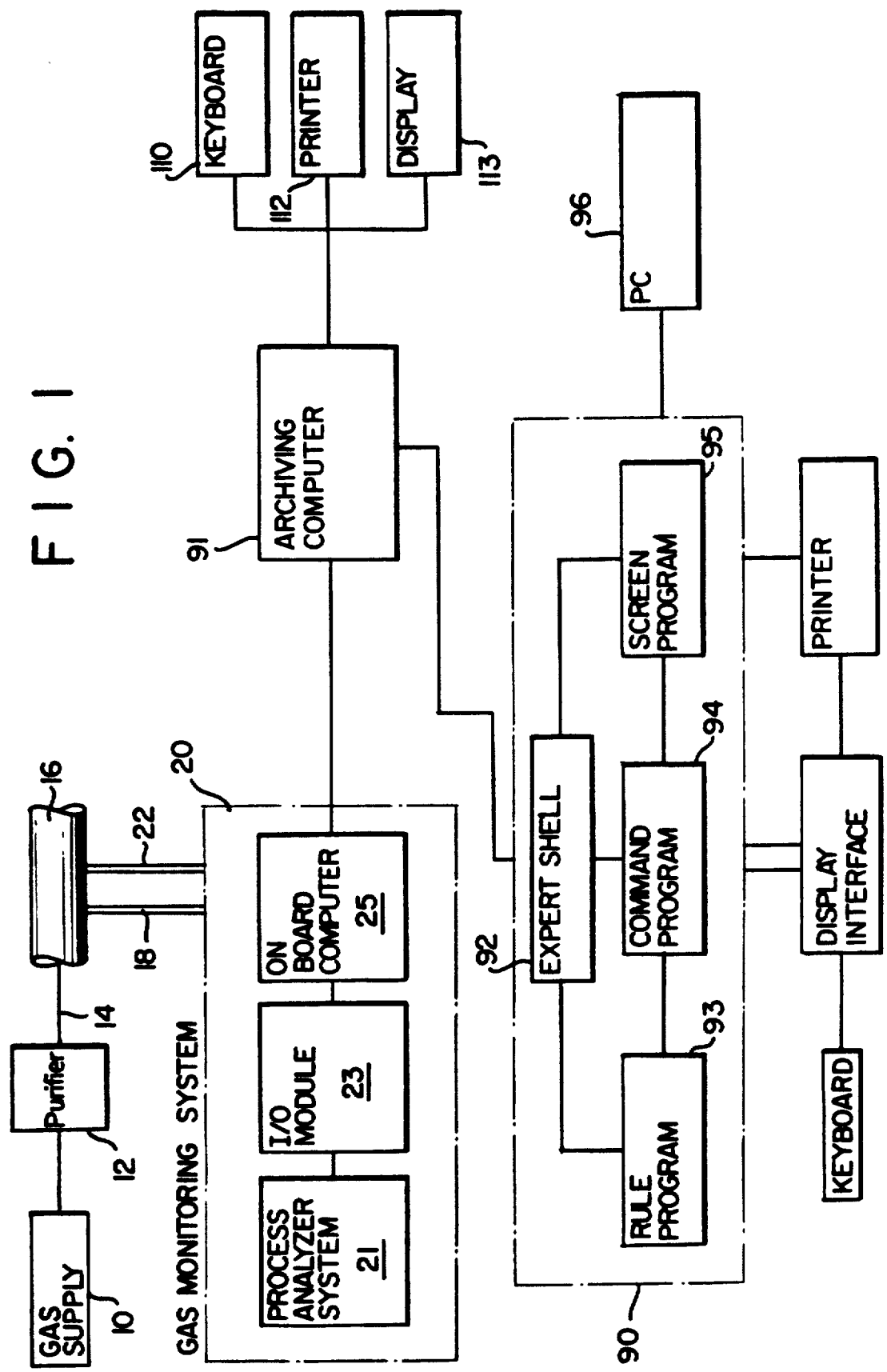

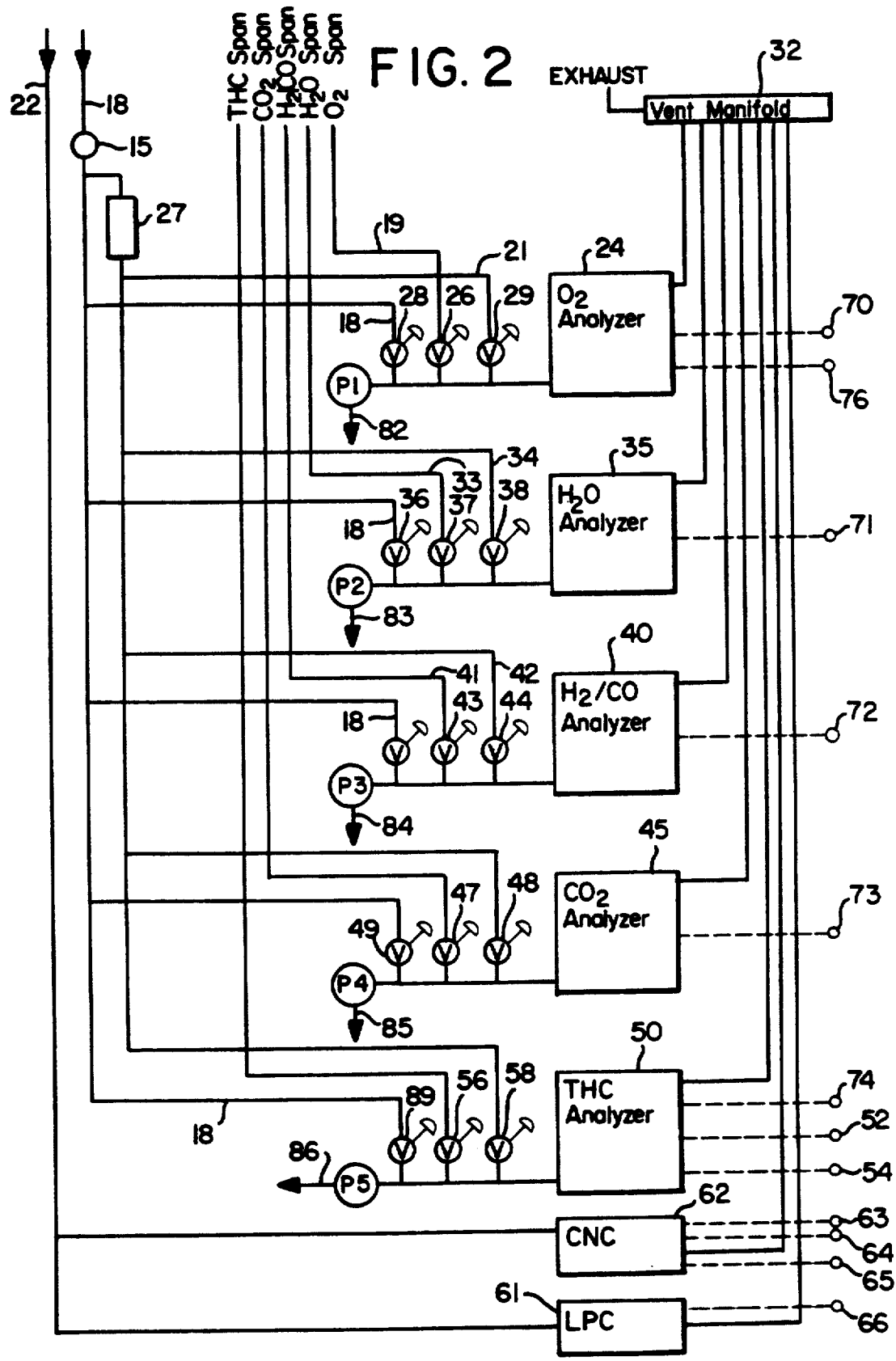

DIAGNOSTIC GAS MONITORING PROCESS UTILIZING AN EXPERT SYSTEM

FIELD OF THE INVENTION

This invention relates to a process for the continuous monitoring of gas flow in a process gas stream and more particularly to a process for analyzing gas impurity levels in a process gas stream and for identifying erroneous conditions of analysis and providing an operator with remedial actions to remedy each erroneous condition.

BACKGROUND OF THE INVENTION

Ultrahigh purity gases are extremely important in the manufacture of many materials and devices such as state of the art semiconductors and optical fibers. The properties of these devices are so critically dependent upon the absolute purity of the process gases that successful manufacture requires continuous monitoring for impurities in the process gas stream. Reducing gases such as hydrogen and carbon monoxide are examples of impurities that may be present in a process gas stream of, for example, nitrogen. These impurities, most notably carbon monoxide, are present in bulk liquid nitrogen. Nitrogen, from an on-site plant, will contain low levels of hydrogen and carbon monoxide. From the prospective of the semiconductor manufacturer trace impurity levels as low as 200 parts per billion (ppb) of a contaminant representing either a gaseous impurity or solid Particulates is significant and detrimental to the manufacturing process. At these contaminant levels of impurity conventional process analyzers require considerable operator skill and expertise to evaluate the data. The operator must have considerable experience in the areas of instrument fault diagnosis, analyzer calibration and data analysis to evaluate the data generated by conventional analyzers in order to distinguish between data identifying a "real" problem from data which is simply erroneous.

Continuous monitoring of process gases currently involves the use of discrete analyzers to monitor impurities of interest. An analysis system for monitoring a feed gas stream within a process reactor is taught and described in U.S. Pat. No. 4,891,186 the disclosure of which is incorporated herein by reference. The system employs a plurality of gas analyzers for separately analyzing individual gas samples from a feed gas stream and includes flow control valves to direct gas samples for individual analysis and to discharge the gas samples that are not being analyzed. A typical analytical system may also include a computer for data acquisition and display.

Although sophisticated analytical equipment is commercially available for impurity detection in a process gas stream at the impurity levels of interest the capability to distinguish process upsets from analyzed phenomenon without extensive operator intervention is severely limited. Any undetected increase in trace impurities in the process gas can be extremely detrimental and an "apparent" increase in trace impurities from extraneous events or momentary "glitches" in data transmission can be even more detrimental in that the manufacturing operation may have to be shut down to correct the non-existent problem. A false or "apparent" problem may be due to a computer or analyzer malfunction, improper calibration, operation outside of design parameters or simply incorrect data analysis. In essence, the ability to assess the validity of analytical data, generated from commercially available process analyzers, is as important as the analytical data itself.

The present invention relates to a process for the continuous analysis of trace contaminants in a process gas stream of $O_2$, N, Ar or $H_2$ and for identifying, storing and recording data representative of such trace contaminants in the process gas stream, for analyzing the stored data to identify erroneous analysis data and for identifying remedial actions to remedy the conditions causing said erroneous analysis data. The process broadly comprises the steps of:

sampling a process gas stream to provide a stream of sample gas;

passing the stream of sample gas through a plurality of analyzers to determine the presence of one or more trace contaminants selected from the group consisting of $O_2$, $H_2$, CO, $CO_2$, hydrocarbons, moisture ($H_2O$) and particulate matter;

generating an output signal for each analyzer corresponding to the level of impurity for each trace contaminant in the process gas stream;

generating a status signal representative of preselected parameters of analyzer operation corresponding to the operating status of one or more of said analyzers;

transferring said status signals and output signals to a computer for storage in the form of data values;

analyzing said data values for the existence of a problem using an expert system rule base program consisting of a multiplicity of rules arranged to form statements corresponding to different problems;

executing said rule base program using an expert system shell with each problem recognized when said data values fall outside defined limits or are not present, storing a file of remedial actions for a preselected number of problem conditions;

directing the expert shell to select the examination of the rules in the rule base program in a predetermined hierarchy and in a linear sequence; and matching problems identified by execution of said rule base program with preselected remedial actions in said remedial action file.

BRIEF DESCRIPTION OF THE DRAWINGS

FIG. 1 is an overall schematic block diagram of the diagnostic gas monitoring system of the present invention;

FIG. 2 is a more elaborate block diagram of the impurity analyzer module of FIG. 1;

DESCRIPTION OF THE PREFERRED EMBODIMENT

Figure 3A:
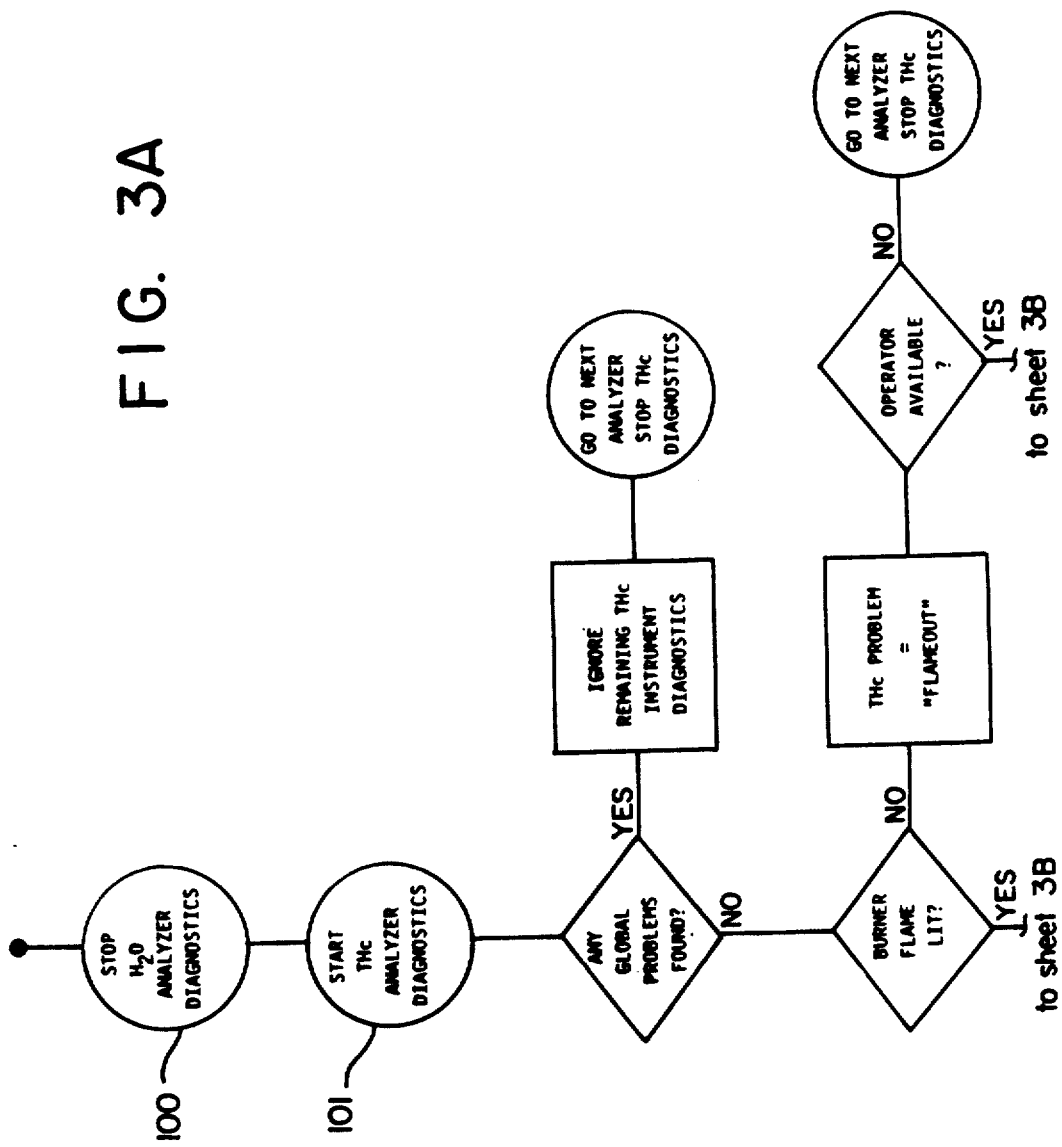
FIGS. 3A to 3F represent a logic flow chart of the rule base program for diagnosing analytical data from a flame ionization detector relative to the hydrocarbon impurity analyzer.
Figure 3B:
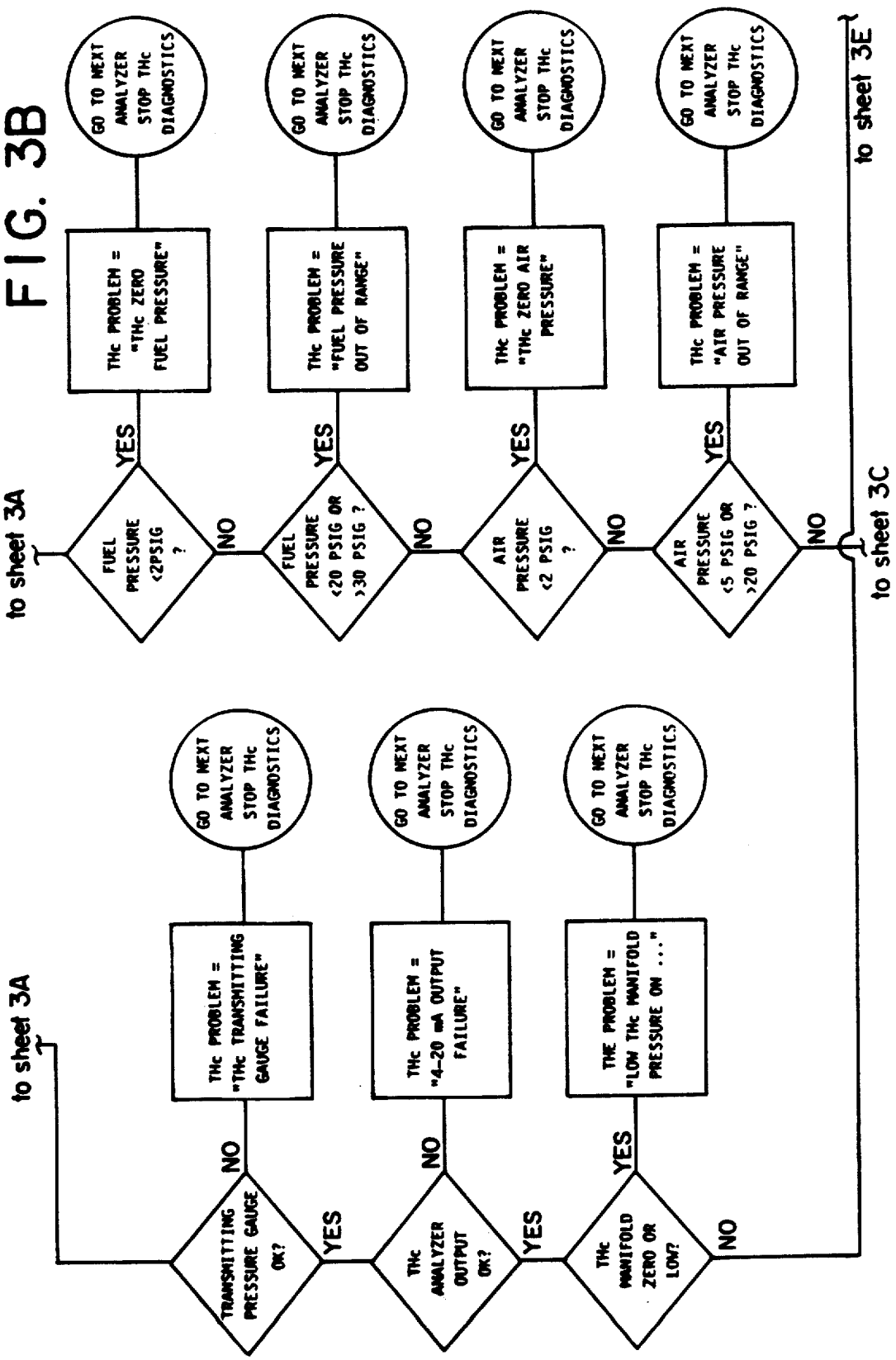
Figure 3C:
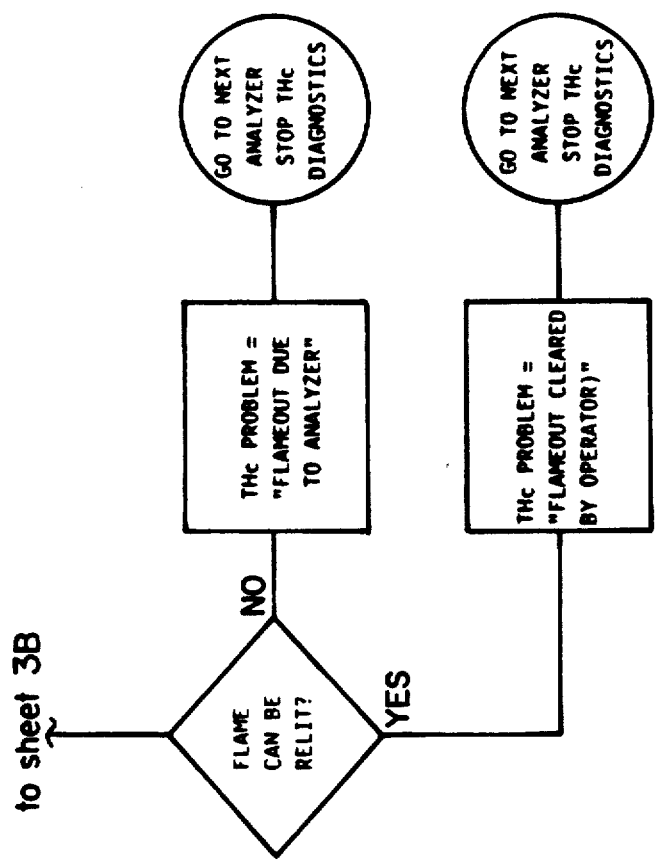
Figure 3D:
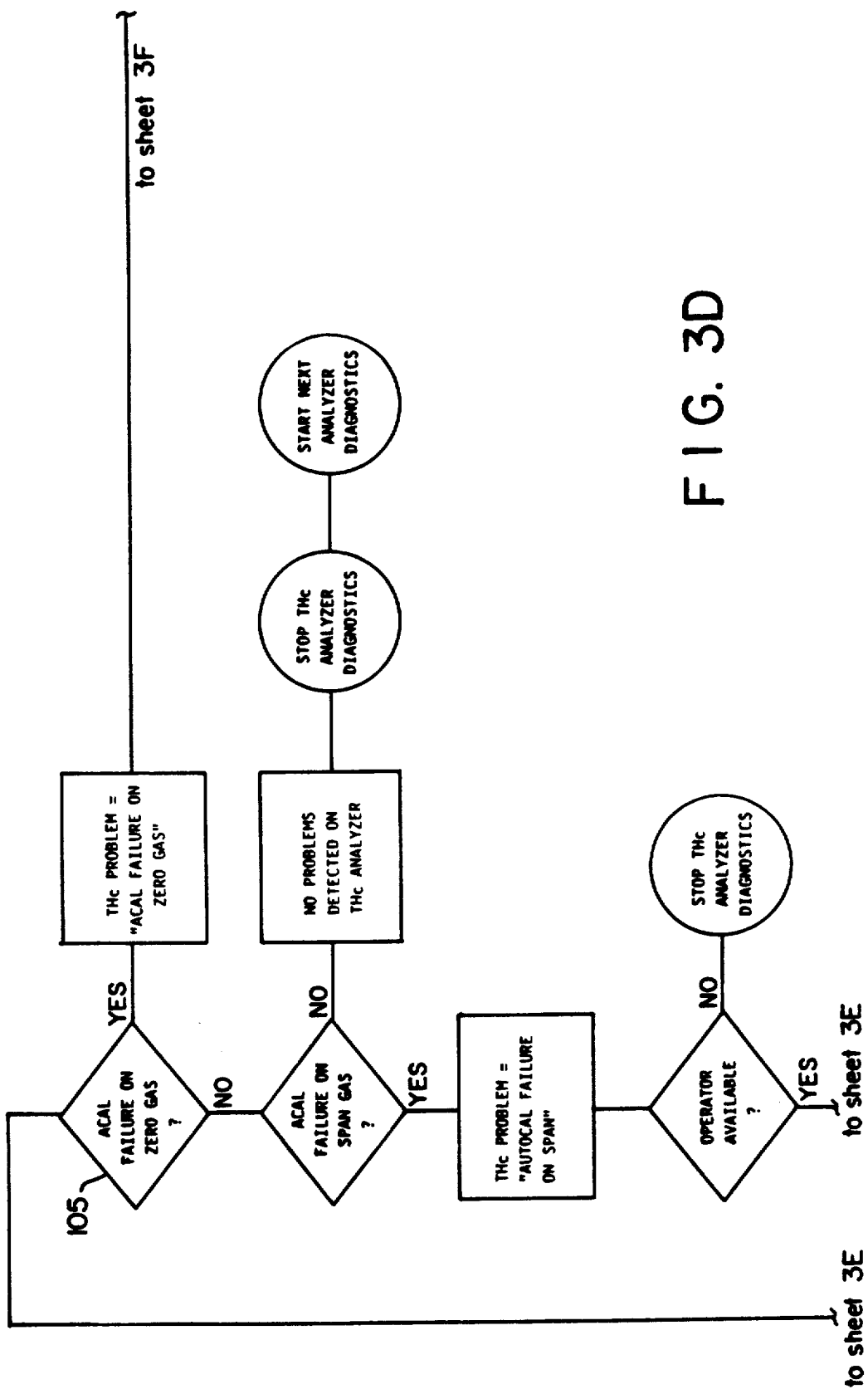

As shown in FIGS. 1 and 2 of the drawings, a supply of bulk gas 10 derived from an on-site plant or bulk gas tank (not shown) is fed through a purifier 12 to form a supply of high purity gas 14 which is delivered through a supply line 16 as product to a customer's facility. The high purity gas 14 includes one or more gases such as, for example, nitrogen, oxygen, argon and hydrogen. Typical impurities can include water, oxygen, carbon monoxide, carbon dioxide, hydrogen, hydrocarbons and particulate matter. The particulate matter may represent suspended solids such as metallic particles or dust. The presence of hydrocarbons may be due to the solvent used for cleaning the cryogenic machinery which generate the high purity gases or the distribution piping. The gas impurities should be detectable at levels below one ppm with the particulate matter detectable at 0.02 microns.

A gas sample 18 is withdrawn from the supply line 16 for analysis in the gas monitoring system 20. Likewise a second gas sample 22 is withdrawn from the supply line 16 for analysis of particulate matter. A pressure regulator 15 is used to regulate the pressure of the gas sample stream 18. The gas monitoring system 20 includes a process analyzer system 21, an I/O module 23 and an on-board computer 25. The process analyzer system 21, as shown in more detail in FIG. 2, includes a multiple number of process analyzers 24, 35, 40, 45, 50, 61 and 62 with each dedicated to analyze for a specific trace contaminant with the exception of hydrogen and carbon monoxide in which the analysis is shared by the single analyzer 45. Process analyzers are commercially available for the detection of water moisture, oxygen, carbon monoxide, carbon dioxide, hydrogen, hydrocarbons and particulates.

The oxygen analyzer 24 as shown in FIG. 2 can be, for example, a commercially available oxygen process analyzer incorporating an electrochemical transducer which uses an aqueous electrolyte specific to oxygen such as the Teledyne oxygen analyzer available from Teledyne Inc. The electrochemical cell acts like a small battery in which the oxygen reacts chemically and causes a small amount of current to flow. The flow of current between the cathode and anode in the electrolyte is directly proportional to the oxygen concentration. Calibration of the analyzer is accomplished by passing a sample of "span gas" 19 and a sample of "zero gas" 21 through the $O_2$ analyzer 24 in substitution for the gas sample 18. "Span gas" is a gas sample from a fixed supply such as a cylinder having a fixed level of gas impurity. The span gas is used as the standard for calibrating the analyzer 24. A different span gas sample is used as a standard for each analyzer in the gas monitoring system 20. The delivery of span gas is controlled by a shut-off valve 26. The shut-off valve 26 is solenoid controlled from the on-board computer 25 or may be separately controlled by an operator. The sample of "zero gas" 21 which is derived by passing the gas sample 18 through a getter 27 to produce a purified gas sample. The zero impurity gas sample 21 is fed to the $O_2$ analyzer 24 under the control of the shut-off valve 29. The operation of the span gas shut-off valve 26 and the zero gas shut-off valve 29 is controlled by the on-board computer 25 in the gas monitoring system 20. The calibrating span and zero gas samples are fed in sequence and in predetermined time intervals for calibrating the analyzer 24 in accordance with a calibration program which does not form a part of the present invention. All of the other analyzers in the gas monitoring system 20 are fed calibration samples of span and zero gas through shut-off valves in a manner substantially identical to that for the $O_2$ analyzer 24 under the control of the computer 25. When the calibration sequence is complete the gas sample 18 is fed to each analyzer under the control of the on-board computer. The gas sample 18 fed to the oxygen analyzer 24 is controlled by the shut-off valve 23. The sample gas stream 18 is exhausted through the vent manifold 32.

For moisture analysis, a commercially available moisture analyzer 35 may be used such as the DuPont 5700 available through the DuPont Corporation. The analyzer 35 is a microprocessor controlled instrument that can measure trace concentrations of water vapor in liquid-free gases. The sensor is a piezoelectric crystal oscillator coated with a thin hydroscopic film. A second uncoated crystal oscillator is used as a reference. When moisture comes in contact with the working crystal it changes the coating mass which dampens the radio frequency at which the working crystal is set. Every 30 seconds a gas sample is alternated with a dry reference gas through the crystal to establish a delta value between the dry and wet values. The frequency of the working crystal is mixed with the reference crystal to form a total oscillation signal which is proportional to the moisture content. This is converted into a ppm reading by a microprocessor. The supply of the $H_2O$ span and zero gas calibration samples 33 and 34 are controlled through the solenoid shut-off valves 37 and 38 respectively. The gas sample stream 18 is controlled through solenoid shut-off valve 36.

The $H_2$/CO analyzer 40 is a commercially available shared analytical reduction gas analyzer which consists of a microprocessor controlled gas chromatograph in which gas sample components are separated chromatographically within a column oven and passed into a heated mercuric oxide bed to form a reaction in which mercury vapor is generated. The mercury vapor is passed through an ultraviolet photometer to measure the reaction. The $H_2$/CO analyzer 40 is calibrated with a span and zero gas sample 41 and 42 through solenoid controlled shut-off valves 43 and 44 respectively with the gas sample stream 18 fed through solenoid controlled shut-off valve 46.

The $CO_2$ analyzer 45 is a nondispersive infra-red analyzer commercially available from the Horiba Corporation. The analyzer operates on a cross flow modulation technique which incorporates a rotary valve to alternately direct sample gas and a high purity reference gas such as $N_2$ to the cells in the analyzer. The amount of infrared energy absorbed by the cells is translated into an output signal which is a measure of the concentration of $CO_2$ between the sample gas and the reference gas. For calibration a span and zero gas sample is fed through solenoid controlled valves 47 and 48 under control of the computer 25. The gas sample 18 is supplied through the solenoid controlled valve 49.

The presence of hydrocarbons in the gas sample stream 18 is detected using a flame-ionization total hydrocarbon analyzer "THC" 50. A preferred THC hydrocarbon analyzer is the Beckman 400A which is commercially available from Beckman Instruments. Sensing is performed by passing a regulated flow of the sample gas stream 18 through a burner flame. Ionization of the sample stream hydrocarbon components occurs as the stream is heated by the flame producing electrons and positive ions. The ions are collected by polarized electrodes creating a current in the electronic measuring circuit. This current is proportional to the rate that carbon atoms enter the flame (hydrocarbon count) and is converted into a digital readout 52 as a measure of hydrocarbon concentration in the sample gas. The analyzer 50 also contains an automatic fuel shut-off valve (not shown) in the event of a flame out. A flame out status signal 54 is generated to identify a flame out fault condition. Span and zero gas samples are supplied to the "THC" total hydrocarbon analyzer 50 through solenoid operated shut-off valves 56 and 58 with the sample gas stream 18 fed through shut-off valve 89.

A separate gas sample 22 is taken from the supply line 16 to analyze for particulate matter. The gas sample 22 is fed to the analyzer system particle counters including a standard laser particle counter "LPC" 61 and a condensation nucleus counter "CNC" 62 with both operated in parallel. The laser counter 61 is a standard light scattering based particle counter utilizing a passive cavity laser for counting particles above 0.1 microns in size and for sizing the particles counted.

The condensation nucleus counter 62 counts each particle down to 0.02 microns in size at a fixed sampling rate.

Particle count data from the condensation nucleus counter 62 is provided as a pulse output 63 with one pulse corresponding to each particle count. Additional analog outputs 64 and 65 from the condensation nucleus counter 62 identify the sampling flow rate and the instrument status respectively.

The laser counter 61 directly provides digital information 66 to the on board computer 25 via a conventional RS-232C port. The status information 66 identifies the laser output reference voltage, instrument temperature and flow/no flow fault status in addition to the particulate count data.

Each of the gas analyzers 24, 35, 40, 45 and 50 respectively provide analog output signals 70, 71, 72, 73 and 74 representative of the impurity levels of each of the analyzed gases. The gas analyzers may also provide status output signals to identify a specific fault condition in connection with the analyzer. For example, the O₂ analyzer 24 provides a status output signal 76 which indicates whether the O₂ analyzer is operating in the designed range of operation. Operation outside the range is a fault condition. The analog output signals 70, 71, 72, 73 and 74 are fed as variable voltage signals through the input/output interface module 23 which includes an analog to digital converter (not shown) for conversion to digital signals (four digit numbers) corresponding to the analog signals. The status input signals from the analyzer and the data input from the particle counters are also fed into the input/output interface module 23. The input/output interface module 23 provides data inputs 81 to the computer 25 for each input channel to the input/output interface 23. In each instance where the instrument can directly generate data in binary form it is fed directly to the computer 25 through a conventional RS-232 port. This is the case for the particle count supplied from the laser particle counter 61. However the condensation nucleus counter output 63 is a pulse signal and the digital status outputs 64 and 65 from the condensation nucleus counter 62 are analog signals representing sampling flow rate and instrument status respectively.

Additional status inputs 82-86 are provided from the pressure gauges P1-P5 for providing a status signal representative of the pressure to each of the gas analyzers 24, 35, 40, 45 and 50 respectively. The status inputs 82-86 are fed to the input/output interface module 23 and transferred in binary format to the on board computer 25. Electrical support utilities (not shown) are also Provided for supplying power to each of the gas analyzers and to the particle counters respectively. The availability of electrical power to each analyzer (not shown) is also provided as a status input signal (not shown) to the input/output interface module 23 and in turn to the on board computer 25. The on board computer 25 is programmed to convert the character information received from the input/output module 23 into corresponding data values which may represent appropriate units of engineering corresponding to the analog information or the status information respectively. The computer 25 assigns a variable or tag name to each data value corresponding to a predetermined location in storage for access by the expert system 90. The data values which correspond to the input data information may be internally stored in the computer 25 or stored in a separate PC computer 91 for data archiving. The conversion of the input data to engineering units is conventional and any number of computer programs are commercially available to perform this operation. The archiving computer may be accessed by the expert system 91 using a dedicated keyboard 110 with its own printer 112 and display 113.

The expert system 91 is a program enhancement that provides the capability to interpret the measured data from the gas analyzers and particle counters and the status inputs to identify and provide remedial action for correcting fault conditions. The expert system 90 includes an expert system shell 92, a rule base program 93, a command program 94 and a screen file 95. Additional support files such as a graphics support program and a data file may also be included. The expert system 90 is preferably programmed for operation on a stand alone PC computer 96 separate from the on board computer 25 and the archiving PC computer 91.

The expert system shell 92 is a commercially available computer program that uses knowledge representations from a knowledge base to reach conclusions normally determined by a human expert. A common form of knowledge representation is in the form of IF . . . THEN rules for any problem that involves a selection from among a definable group of choices where the decision is either TRUE or FALSE based on logical rules. The rules can involve relative probabilities of a choice being correct. The expert system shell 92 incorporates a translator or compiler for executing the language constructs provided by the shell 92 which the shell 92 then converts into a high level computer executable binary language for execution in the computer 96. The shell defines the syntax and structure for the preparation of a knowledge base which is represented by the rule base program in the present invention.

The preferred expert system shell 92 utilized in the practice of the present invention is the "EXSYSP Professional" available from EXSYS Inc. which is a generalized expert system package. In accordance with the present invention the expert system shell 92 operates in response to the command program 94 to execute the rule base program 93. The command program 94 directs the expert system shell 92 to follow a predetermined sequence in implementing the rules, i.e., it identifies the hierarchy for the rules in the rule base program 93 and upon identification of the problems in carrying out the rule base program 93, the command program 94 provides the methodology for the system shell 92 to match the problems identified by the rule base program 94 with a corresponding remedial action in the screen file 95. The screen file 95 is a listing of predefined remedial actions which an operator can use to solve a fault condition identified by a problem. The command program 94 matches the problem identified upon execution of the rule based program with one of the predefined remedial actions in the screen file 95 and directs the remedial action to be displayed on the CRT display 97 if an operator is present and/or prints out the diagnostic information consisting of the list of identified problems in the printer 98. A keyboard 99 is used by an operator to interface with the expert system 90. The command program 94 in the present invention directs the expert system shell 92 to follow a "forward no backward" sequence in implementing the rule base program 93. Accordingly, the expert system shell will execute the rule base program 93 in a linear sequence from the first rule until completion.

The rule base program 93 consists of a multiplicity of rules made up of "IF . . . THEN" statements which assign problems to identify a diagnosis based on whether the "IF . . . THEN" statement is true or false. The diagnosis permits a multiple number of decisions to be made based on the interactions with an operator to lead to a more specific diagnosis of the problem. The IF conditions in the rule base can be "OR" gated or "AND" gated such that a plurality of IF conditions need be satisfied to assign a problem.

FIG. 3 is a logic flow chart of the rule base program for diagnosing problems in the flame ionization total hydrocarbon analyzer (THC) 50. The appropriate section of the rule base program for performing the diagnosis identified in the logic flow chart of FIG. 3 is described below as follows:

Rule Base Program for Hydrocarbon Analyzer

```
RULE NUMBER:  57  (H2O 17)
IF:
        OPERATOR IS AVAILABLE
   and  [H2O PROBLEM] = "H2O ANALYZER SENSITIVITY CHANGE"
   and  [FAULT] = 15
THEN:
        [H2O PROBLEM] IS GIVEN THE VALUE "DUPONT REFERENCE DRYER EXPENDED"

RULE NUMBER:  58  (H2O 18)
IF:
        OPERATOR IS AVAILABLE
   and  [H2O PROBLEM] = "H2O ANALYZER SENSITIVITY CHANGE"
   and  [FAULT] = 17
THEN:
        [H2O PROBLEM] IS GIVEN THE VALUE "DUPONT SAMPLE CELL DAMAGE"

RULE NUMBER:  59  (THC 1)
IF:
        [THC PROBLEM] = "NONE" OR [THC PROBLEM] = "IMPAIRED"
   and  [TSI12] = "ABNORMAL"
THEN:
        [THC PROBLEM] IS GIVEN THE VALUE "FLAMEOUT"

RULE NUMBER:  60  (THC 2)
IF:
        OPERATOR IS AVAILABLE
   and  [THC PROBLEM] = "FLAMEOUT"
   and  [THC FUEL] < 2.
THEN:
        [THC PROBLEM] IS GIVEN THE VALUE "THC ZERO FUEL PRESSURE"
   and  THC FUEL PRESSURE IS ZERO RULE NUMBER:  61  (THC 3)
IF:
        OPERATOR IS AVAILABLE
   and  [THC PROBLEM] = "FLAMEOUT"
   and  [THC FUEL] < 20. or [THC FUEL] > 30.
```

THEN:
        [THC PROBLEM] IS GIVEN THE VALUE "FUEL PRESSURE OUT OF RANGE"
    and    THC FUEL PRESSURE IS OUT OF RANGE RULE NUMBER: 62   (THC 4)
IF:
        OPERATOR IS AVAILABLE
    and    [THC PROBLEM] = "FLAMEOUT"
    and    [THC AIR] < 2.
THEN
        [THC PROBLEM] IS GIVEN THE VALUE "THC ZERO AIR PRESSURE"
    and    THC AIR PRESSURE IS ZERO RULE NUMBER: 63   (THC 5)
IF:
        OPERATOR IS AVAILABLE
    and    [THC PROBLEM] = "FLAMEOUT"
    and    [THC AIR] < 5. or [THC AIR] > 20.
THEN:
        [THC PROBLEM] IS GIVEN THE VALUE "AIR PRESSURE OUT OF RANGE"
    and    THC AIR PRESSURE IS OUT OF RANGE RULE NUMBER: 64   (THC 6)
IF:
        OPERATOR IS AVAILABLE
    and    [THC PROBLEM] = "FLAMEOUT"
    and    THC FUEL PRESSURE IS OK
    and    THC AIR PRESSURE IS OK
    and    FLAME RELIT? ANSWER IS NO
THEN:
        [THC PROBLEM] IS GIVEN THE VALUE "FLAMEOUT DUE TO ANALYZER"

RULE NUMBER: 65   (THC 6A)
IF:
        OPERATOR IS AVAILABLE
    and    [THC PROBLEM] = "FLAMEOUT"
    and    THC FUEL PRESSURE IS OK
    and    THC AIR PRESSURE IS OK
    and    FLAME RELIT? ANSWER IS YES
THEN:
        [THC PROBLEM] IS GIVEN THE VALUE "FLAMEOUT (CORRECTED BY
        OPERATOR)"

RULE NUMBER: 66   (THC 7)
IF:
        [THC PROBLEM] = "NONE"
    and    [PI12] —= -2.5
THEN:
        [THC PROBLEM] IS GIVEN THE VALUE "THC TRANSMITTING GAUGE FAILURE"
NOTE:
    GAUGE HAS AN OPEN CIRCUIT VALUE OF -25 psig BASED ON A 0-100 PSIG
    TRANSMITTER RANGE.

RULE NUMBER: 67 (THC 8)
IF:
       [THC PROBLEM] = "NONE" or [THC PROBLEM] = "IMPAIRED"
  and  [AO12] ~= -2.5
THEN:
       [THC PROBLEM] IS GIVEN THE VALUE "4-20 mA OUTPUT FAILURE"
NOTE:
  BASED ON 4-20 mA EQUIVALENT TO 0-10 PPM RULE NUMBER: 68 (THC 9)
IF:
       [THC PROBLEM] = "NONE"
  and  [PI12] < [PLI12]
THEN:
       THC MANIFOLD PRESSURE IS LOW RULE NUMBER: 69 (THC 10)
IF:
       THC MANIFOLD PRESSURE IS LOW
  and  [PI12] < 2.
THEN:
       CLEAR (Q "THC MANIFOLD")
  and  THC MANIFOLD PRESSURE IS ZERO RULE NUMBER: 70 (THC 11)
IF:
       THC MANIFOLD PRESSURE IS LOW OR ZERO
THEN:
       [THC PROBLEM] IS GIVEN THE VALUE "LOW THC MANIFOLD PRESSURE ON "
       + [THC_VPOS]
NOTE:
  VALVE POSITION DETERMINED AT START OF RUN BY BASIC PROGRAM VPOS RULE NUMBER: 71 (THC 12)
IF:
       [THC PROBLEM] = "NONE"
  and  INT([ZSI102]) = 4.00 OR ABS([ALI12]) > 0.05 OR ABS([AHI12]) > 8.00
THEN:
       THC AUTOCAL HAS FAILED RULE NUMBER: 72 (THC 13)
IF:
       [THC PROBLEM] = "NONE"
  and  THC AUTOCAL HAS FAILED
  and  [ZSI102] = 4.00
THEN:
       [THC PROBLEM] IS GIVEN THE VALUE "THC AUTOCAL FAILURE ON ZERO"

RULE NUMBER: 73 (THC 14)
IF:
       [THC PROBLEM] = "NONE"
  and  THC AUTOCAL HAS FAILED
  and  ABS([ALI12]) > 0.05
THEN:
       [THC PROBLEM] IS GIVEN THE VALUE "THC AUTOCAL FAILURE ON ZERO"

NOTE:
   FAILED IF ZERO CORRECTION EXCEEDS .05 PPM

RULE NUMBER: 74 (THC 15)
IF:
       OPERATOR IS AVAILABLE
   and [THC PROBLEM] = "THC AUTOCAL FAILURE ON ZERO"
   and [PTHC ZERO] < 200.
THEN:
       [THC PROBLEM] IS GIVEN THE VALUE "EMPTY ZERO GAS CYLINDER"
NOTE:
   THC ANALYZER IS ONLY ANALYZER SUPPLIED WITH ZERO GAS FROM A CYLINDER AND
   NOT AN ONBOARD GETTER RULE NUMBER: 75 (THC 16)
IF:
       OPERATOR IS AVAILABLE
   and [THC PROBLEM] = "THC AUTOCAL FAILURE ON ZERO"
   and [PTHC ZERO] > 200.
THEN:
       [THC PROBLEM] IS GIVEN THE VALUE "THC ANALYZER ZERO DRIFT"
NOTE:
   THC ANALYZER IS ONLY ANALYZER SUPPLIED WITH ZERO GAS FROM A CYLINDER AND
   NOT AN ONBOARD GETTER RULE NUMBER: 76 (THC 17)
IF:
       [THC PROBLEM] = "NONE"
   and THC AUTOCAL HAS FAILED
   and [ZSI102] = 4.10
THEN:
       [THC PROBLEM] IS GIVEN THE VALUE "THC AUTOCAL FAILURE ON SPAN"

RULE NUMBER: 77 (THC 17)
IF:
       [THC PROBLEM] = "NONE"
   and THC AUTOCAL HAS FAILED
   and ABS([AHI12]) > 8.00
THEN:
       [THC PROBLEM] IS GIVEN THE VALUE "THC AUTOCAL FAILURE ON SPAN"
NOTE:
   STD BUS REJECT AT 10% EXPERT SYSTEM FLAG AT 8%

RULE NUMBER 78 (THC 19)
IF:
       OPERATOR IS AVAILABLE
   and [THC PROBLEM] = "THC AUTOCAL FAILURE ON SPAN"
   and [PTHC SPAN] < 200.

RULE NUMBER: 79 (THC 20)
IF:
       OPERATOR IS AVAILABLE
   and [THC PROBLEM] = "THC AUTOCAL FAILURE ON SPAN"
   and [PTHC SPAN] > 200.
THEN:
       [THC PROBLEM] IS GIVEN THE VALUE "THC ANALYZER SENSITIVITY CHANGE"

The rule base program is more clearly understood when read in conjunction with the logic flow chart of FIG. 3. The rule base program is executed in a linear sequence with the analysis of the total hydrocarbon analyzer 50 directly following the analysis of the $H_2O$ Analyzer 35. The circle 100 delineates the end of the block of the statements for the $H_2O$ Analyzer 35 and the circle 101 indicates the start of the block of rules for the hydrocarbon analyzer 50. The first statement is identical for all of the analyzer diagnostics. The rules defining the presence of "global problems" overrides the analyzer diagnostics and represents problems not attributable to a specific analyzer or particle counter but rather to a common problem such as low pressure representing a loss of sample flow or lack of utilities which is determined from the status input information to the on board computer. Unless a global problem exists all such problems are initialized to "NONE" permitting the rule base program to proceed in the analysis of the total hydrocarbon analyzer 50. The rule statement NO. 59 identifies an abnormal condition if the burner flame in the hydrocarbon analyzer 50 is not lit and defines the problem as "FLAMEOUT". The process of the present invention determines if a problem exists and provides the operator, if present, with an analysis of the assigned problem in the form of one or more remedial actions to remedy the problem. The command program in conjunction with the screen file of remedial actions performs this function as will be explained in detail further in the specification.

If an operator is not present, which is automatically assumed if execution of the rule base has started at a preset time interval rather than an operator log on, then the rule base program proceeds to the next analyzer in sequence. If the operator is present the affirmative answer to a more specific diagnosis determined from a dialog with the operator based upon the response to specific technical questions relating to e.g., fuel pressure and air pressure permits the problem to be more specifically diagnosed with the more specific diagnosis identified as the conclusory hydrocarbon problem (THC PROBLEM) before proceeding to the next analyzer.

If the burner flame is lit the rule base program decides if the appropriate pressure gauge is operational based upon data values stored in the computer corresponding to gauge pressure and, if not, assigns the problem 'THC TRANSMITTING GAUGE FAILURE" before proceeding to the next analyzer. If no THC problem exists the rule base program decides if the THC analyzer output is within range based also on data values stored in the computer corresponding to the analog input from the analyzer providing such information and, if not, assigns the analyzer output range as the problem. If no THC problem is found the next succeeding rule is to decide if the analyzer manifold pressure is low from stored data values corresponding to the analyzer manifold pressure and if not the rule base program proceeds to determine if "autocalibration" has failed on zero gas. Autocalibration designates an automatic calibration sequence which is under the control of the on board computer 25 pursuant to a calibration program the operation of which, of itself, is not part of the present invention. As explained earlier a sample of span gas and a sample of zero gas is fed into each analyzer in place of the sample gas for purposes of calibrating each of the analyzers 24, 35, 40, 45 and 50 respectively. Each analyzer should provide a predictable response to the span gas sample and to the zero gas sample respectively which can be readily diagnosed to maintain each of the analyzers properly calibrated. The expert system of the present invention determines if the autocalibration operation has failed and diagnosis the failure to identify the problems which most likely exist at the conclusion of the diagnosis. Thus, as indicated in the logic flow diagram of FIG. 3D, the decision box 105 establishes the existence of autocalibration failure first with zero gas and, if so, assigns failure on zero gas as the problem. This corresponds to RULE NUMBER 71 in the rule base program where the variable or tag name designation "ZSI102" defines the autocalibration status with the variable integer in the tag name identifying which, if any, of the analyzers has failed autocalibration. The digits following the integer identifies whether a failure has occurred or zero or span gas. If failure has indeed occurred then an inquiry decision is made to determine the presence of the operator. The operator must respond for the rule base program to provide a further diagnosis. Otherwise, the rule base program will proceed to the next analyzer leaving the problem identified as autocalibration failure on zero gas. If an operator is present and responds affirmatively the rule base program communicates with the operator in a dialog to pinpoint the problem resulting from the autocalibration failure as either resulting e.g. from an empty cylinder or zero drift. In either case the rule base program does not provide remedial action. This is provided by the command program.

If the autocalibration did not fail on zero gas the rule base program proceeds to decide if the autocalibration has failed on span gas. The diagnosis is similar to that conducted for zero gas by first inquiring as to the presence of an operator. If an operator is present the rule base program communicates with the operator in a dialog to pinpoint the problem before proceeding to the next analyzer.

The rule base program proceeds in a logical and predetermined sequence seeking to identify the existence of a problem and to further diagnose the problem to a logical conclusion. Once a problem is found and its diagnosis identified the rule base program proceeds to the next analyzer or particle counter to perform a similar analysis. Accordingly, if an autocalibration span gas problem is found, the diagnosis terminates after the problem is pinpointed.

Figure 3E:
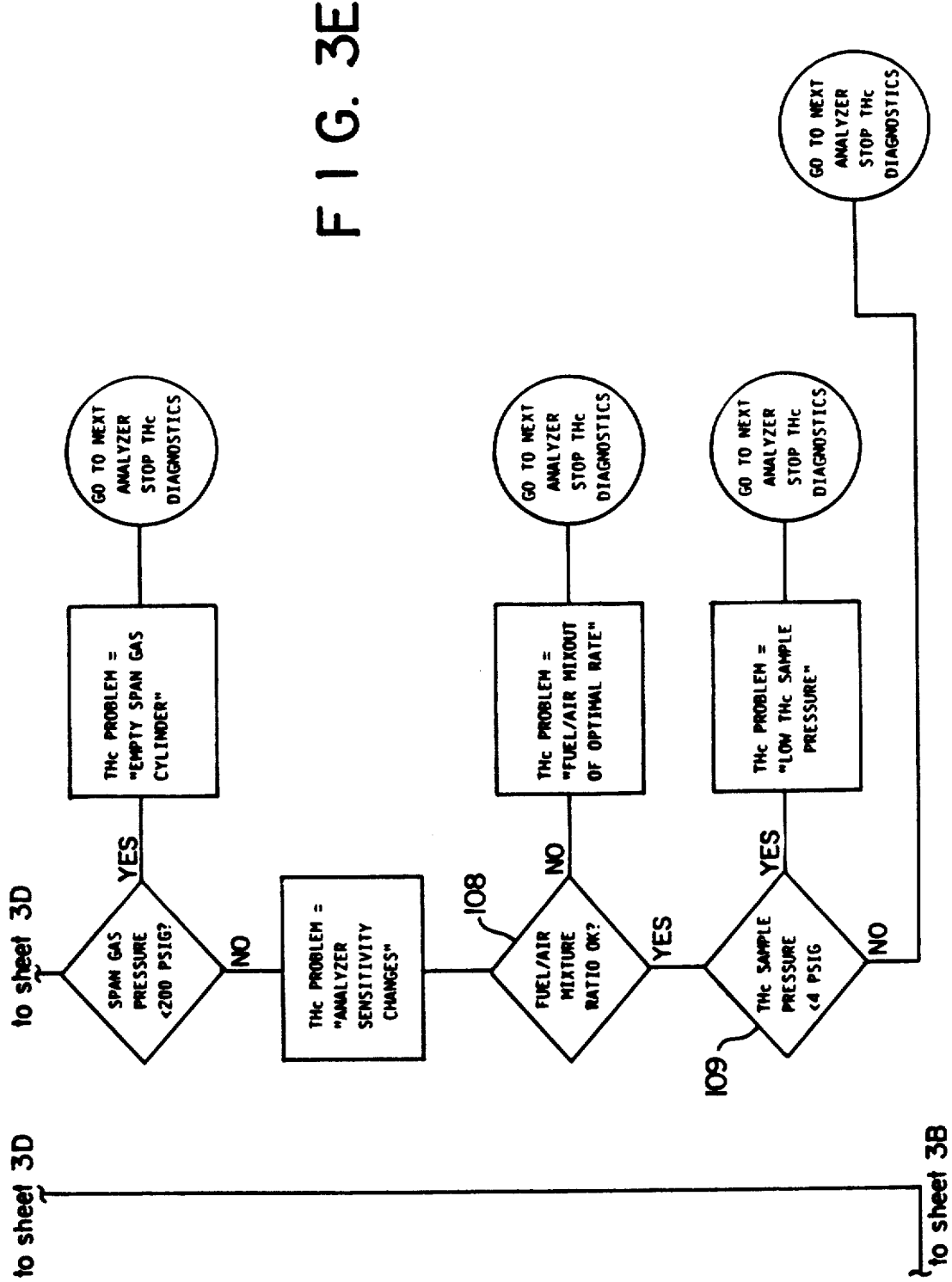
Figure 3F:
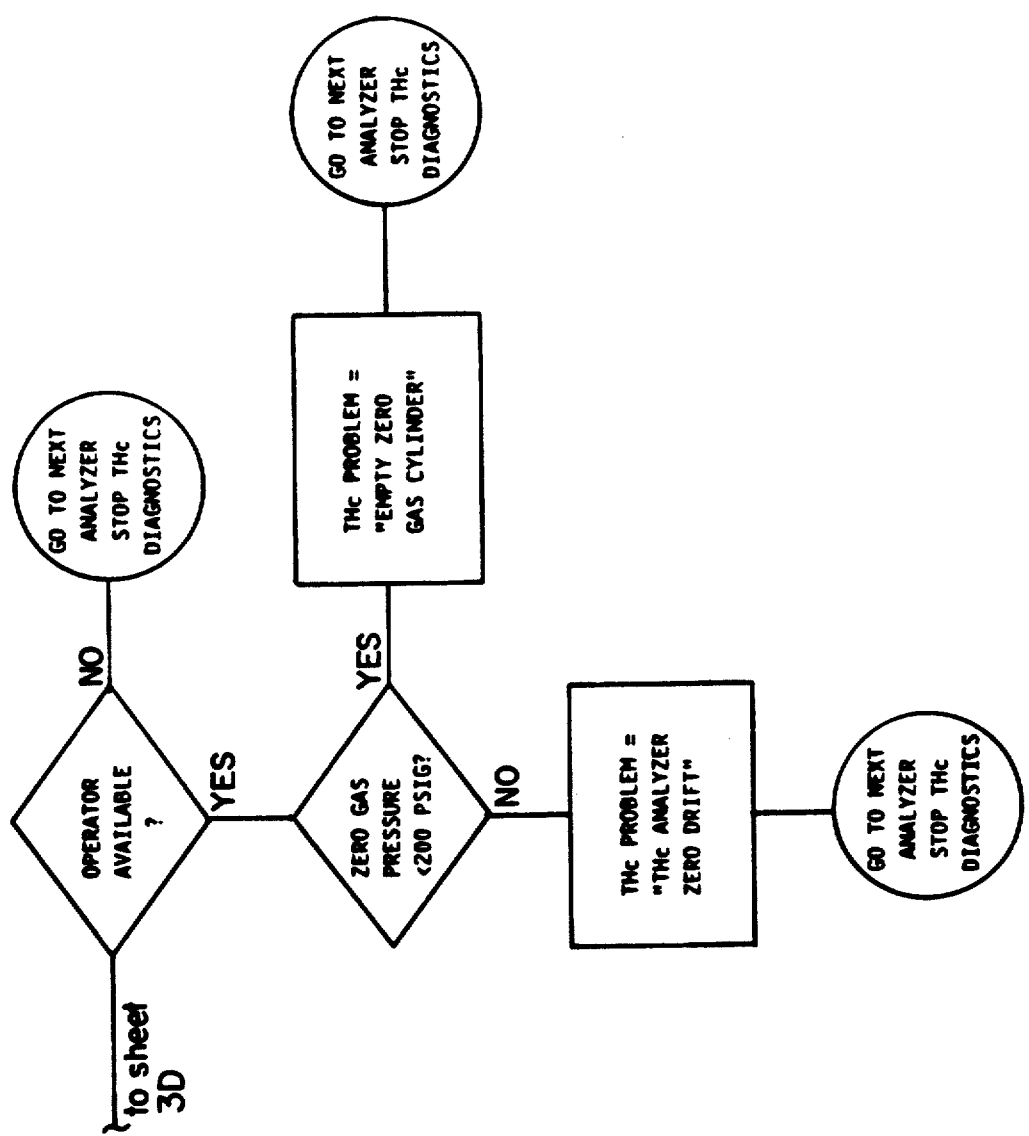

For example, if an analyzer sensitivity change problem is found the rule base program proceeds as indicated in FIG. 3E to further diagnose the problem by proceeding to the next decision box 108 to decide if the fuel/air mixture to the hydrocarbon analyzer is proper and, if not, identifies this as the problem. If the fuel/air mixture ratio is correct the rule base program proceeds to the last decision box 109 to decide if the sample gas pressure is too low. If the sample pressure is low this is identified as the problem before proceeding to the next analyzer. If no problems are discovered the problem remains at a value of "NONE" and the rule base proceeds to the next analyzer.

The execution of the rule base program occurs upon command under the direction of the command program 94. The logic flow diagram for the command program 94 is shown in the flow chart of FIGS. 4A and 4B and the following is an exerpt from the command program for directing the shell to carry out the process of the present invention as it applies to some examples of global problems and to the handling of remedial action for the total hydrocarbon analyzer 50:

COMMAND PROGRAM:

```
/*
:START  /*STARTING POINT FOR ALL RUNS OF SANPAVAT
/*
/* EXECUTIVE TIMER PROGRAM HERE
RUN INMENU /D
/*
IF [X] = "1000"
ASK [INTRO]
GOTO START
ENDIF
/*
IF [X] = "3000"
DISPLAY PROBLEMS.LOG
GOTO START
ENDIF
/*
IF [X] = "4000"
ASK [BTCHAN]
GOTO START
ENDIF
/*
IF [X] = "5000"
ASK [BTCFG]
GOTO START
ENDIF
/*
IF [X] = "6000"
ASK [BTNOP]
GOTO START
ENDIF
/*
IF [X] = "7000"
ASK [MANUAL]
GOTO START
ENDIF
/*
IF [X] = "8000"
CMDFILE DIGIT
GOTO START
ENDIF
/*
IF [X] = "25000"
RUN CLEANUP [DA2] /B /C
GOTO START
ENDIF
/*
IF [X] = "9000"
ASK [D]
IF [D] = "N" OR [D] = "n"
GOTO START
ENDIF
GOTO FINISH
ENDIF
/*
/*   ABORT ON MISSED DATA SCAN
```

```
/*
RULES 1-2
IF [GLOBAL PROBLEM] = "MISSED DATA SCAN FROM STD BUS"
GOTO START
ENDIF /* ABORT
/*
/* COMMAND LANGUAGE TO DETERMINE ANALYZER MANIFOLD POSITIONS
/*
RUN VPOS 402 [SI917D] [SI917E] [SI917C] / D
/*
RUN VPOS 302 [SI910D] [SI910E] [SI910C] / D
/*
RUN VPOS H2O [SI911D] [SI911E] [SI911C] / D
/*
RUN VPOS THC [SI912D] [SI912E] [SI912C] / D
/*
RUN VPOS RGA [SI913D] [SI913E] [SI913C] / D
/*
RUN VPOS CO2 [SI914D] [SI914E] [SI914C] / D
/*
/* COMMAND LANGUAGE FOR STAND ALONE OPERATION
/*
IF [NAME] = "NOBODY"
RULES 3-143  /F /N
RUN DAYTIME /D /* GET DATE AND TIME FOR REPORT HEADER TIMESTAMP
REPORT SANFAVAT.OUT
GOTO REPLOOP /* RESET FOR NEXT PASS THROUGH EXPERT SYSTEM
ENDIF /* STAND ALONG OPERATION
/*
/* RUN RULES FOR OPERATOR ASSISTED PASS THROUGH EXPERT SYSTEM
RULES 3-154 /F /N
/*
/* COMMAND LANGUAGE FOR CONTROL OF REMEDIAL ACTION DISPLAY FILES
/*    IMPLEMENTED WITH OPERATOR ASSIST ONLY
/*
/* REMEDIAL ACTION FILES FOR GLOBAL PROBLEMS
/*
IF [GLOBAL PROBLEM] = "24 V POWER SUPPLY FAILURE IN LEFT HAND
GMS PANEL"
:LB1
ASK [LGMS_24V]
IF [LGMS_24V] = "G" OR [LGMS_24V] = "g"
RUN SLIDE C:\DIGITAL\POWER.PCX /C
GOTO LB1
ENDIF    /* GRAPHICS LOOP
ENDIF    /* CURRENT PROBLEM
/*
IF [GLOBAL PROBLEM] = "24 V POWER SUPPLY FAILURE IN RIGHT HAND
GMS PANEL"
:LB2
ASK [RGMS_24V]
IF [RGMS_24V] = "G" OR [RGMS_24V] = "g"
RUN SLIDE C:\DIGITAL\POWER.PCX /C
GOTO LB2
ENDIF    /* GRAPHICS LOOP
ENDIF    /* CURRENT PROBLEM
/*
IF [GLOBAL PROBLEM] = "4N2 O2 TRANSMITTING GAUGE FAILURE"
```

```
:LB2A
ASK [P402_420]
IF [P402_420] = "G" OR [P402_420] = "g"
RUN SLIDE C:\DIGITAL\PATOD.PCX /C
GOTO LB2A
ENDIF    /* GRAPHICS LOOP
ENDIF    /* CURRENT PROBLEM
/*
IF [GLOBAL PROBLEM] = "LOW GMS PANEL PRESSURE ON 4N2 SAMPLE
STREAM"
:LB3
ASK [4N2_LPP]
IF [4N2_LPP]= "G" OR [4N2_LPP]= "g"
RUN SLIDE C:\DIGITAL\RHTUBE.PCX /C
RUN SLIDE C:\DIGITAL\SAM4N2.PCX /C
GOTO LB3
ENDIF    /* GRAPHICS LOOP
ENDIF    /* CURRENT PROBLEM
/*
IF [GLOBAL PROBLEM] = "LOW GMS PANEL PRESSURE ON 3N2 SAMPLE
STREAM"
:LB4
ASK [3N2_LPP]
IF [3N2_LPP]= "G" OR [3N2_LPP]= "g"
RUN SLIDE C:\DIGITAL\RHTUBE.PCX /C
RUN SLIDE C:\DIGITAL\SAM3N2.PCX /C
GOTO LB4
ENDIF    /* GRAPHICS LOOP
ENDIF    /* CURRENT PROBLEM
/*
IF [GLOBAL PROBLEM] = "12 VOLT POWER SUPPLY FAILURE IN RIGHT
HAND GMS"
:LB5
ASK [GMS_12V]
IF [GMS_12V] = "G" OR [GMS_12V] = "g"
RUN SLIDE C:\DIGITAL\POWER.PCX /C
GOTO LB5
ENDIF    /* GRAPHICS LOOP
ENDIF    /* CURRENT PROBLEM
/*
IF [GLOBAL PROBLEM] = "LOW INSTRUMENT AIR PRESSURE"
ASK [GMS_LIA]
ENDIF    /* CURRENT PROBLEM
/*
IF [PURIFIER PROBLEM] = "PURIFIER ALARM"
ASK [ANYPURE]
ENDIF    /* CURRENT PROBLEM
/*
IF [PURIFIER PROBLEM] = "LOW DISCHARGE PRESSURE"
ASK [PRESPURE]
ENDIF    /* CURRENT PROBLEM
/*
   ( REMEDIAL ACTION FILES FOR SEVERAL ANALYZERS NOT SHOWN  )
/*
/* REMEDIAL ACTION FILES FOR THE THc ANALYZER
/*
IF [THC PROBLEM] = "FUEL PRESSURE OUT OF RANGE"
:LB28
```

```
ASK [THC_LF]
IF [THC_LF] = "G" OR [THC_LF] = "g"
RUN SLIDE C:\DIGITAL\FLOW400.PCX /C
RUN SLIDE C:\DIGITAL\THCINT.PCX /C
GOTO LB28
ENDIF    /* GRAPHICS LOOP
ENDIF    /* CURRENT PROBLEM
/*
IF [THC PROBLEM] = "THC ZERO FUEL PRESSURE"
:LB29
ASK [THC_NF]
IF [THC_NF] = "G" OR [THC_NF] = "g"
RUN SLIDE C:\DIGITAL\FLOW400.PCX /C
RUN SLIDE C:\DIGITAL\THCINT.PCX /C
RUN SLIDE C:\DIGITAL\SOLENOID.PCX /C
GOTO LB29
ENDIF    /* GRAPHICS LOOP
ENDIF    /* CURRENT PROBLEM
/*
IF [THC PROBLEM] = "AIR PRESSURE OUT OF RANGE"
:LB31
ASK [THC_LA]
IF [THC_LA] = "G" OR [THC_LA] = "g"
RUN SLIDE C:\DIGITAL\FLOW400.PCX /C
RUN SLIDE C:\DIGITAL\THCINT.PCX /C
GOTO LB31
ENDIF    /* GRAPHICS LOOP
ENDIF    /* CURRENT PROBLEM
/*
IF [THC PROBLEM] = "THC ZERO AIR PRESSURE"
:LB32
ASK [THC_NA]
IF [THC_NA] = "G" OR [THC_NA] = "g"
RUN SLIDE C:\DIGITAL\FLOW400.PCX /C
RUN SLIDE C:\DIGITAL\THCINT.PCX /C
GOTO LB32
ENDIF    /* GRAPHICS LOOP
ENDIF    /* CURRENT PROBLEM
/*
IF [THC PROBLEM] = "FLAMEOUT DUE TO ANALYZER"
:LB33
ASK [THC_FOUT]
IF [THC_FOUT] = "G" OR [THC_FOUT] = "g"
RUN SLIDE C:\DIGITAL\FLOW400.PCX /C
RUN SLIDE C:\DIGITAL\BURNER.PCX /C
GOTO LB33
ENDIF    /* GRAPHICS LOOP
ENDIF    /* CURRENT PROBLEM
/*
IF [THC PROBLEM] = "TRANSMITTING GAUGE FAILURE"
:LB34
ASK [PTHC_420]
IF [PTHC_420] = "G" OR [PTHC_420] = "g"
RUN SLIDE C:\DIGITAL\PATOD.PCX /C
GOTO LB34
ENDIF    /* GRAPHICS LOOP
ENDIF    /* CURRENT PROBLEM
/*
```

```
IF [THC PROBLEM] = "4-20 mA OUTPUT FAILURE"
:LB35
ASK [THC_420]
IF [THC_420] = "G" OR [THC_420] = "g"
RUN SLIDE C:\DIGITAL\ATOD.PCX /C
GOTO LB35
ENDIF    /* GRAPHICS LOOP
ENDIF    /* CURRENT PROBLEM
/*
IF [THC PROBLEM] = "LOW THC MANIFOLD PRESSURE ON ZERO"
:LB36
ASK [THC_ALPZ]
IF [THC_ALPZ] = "G" OR [THC_ALPZ] = "g"
RUN SLIDE C:\DIGITAL\IMOD.PCX /C
RUN SLIDE C:\DIGITAL\VALVE.PCX /C
GOTO LB36
ENDIF    /* GRAPHICS LOOP
ENDIF    /* CURRENT PROBLEM
/*
IF [THC PROBLEM] = "LOW THC MANIFOLD PRESSURE ON SPAN"
:LB37
ASK [THC_ALPS]
IF [THC_ALPS] = "G" OR [THC_ALPS] = "g"
RUN SLIDE C:\DIGITAL\IMOD.PCX /C
RUN SLIDE C:\DIGITAL\VALVE.PCX /C
GOTO LB37
ENDIF    /* GRAPHICS LOOP
ENDIF    /* CURRENT PROBLEM
/*
IF [THC PROBLEM] = "LOW THC MANIFOLD PRESSURE ON SAMPLE"
:LB38
ASK [THC_ALPM]
IF [THC_ALPM] = "G" OR [THC_ALPM] = "g"
RUN SLIDE C:\DIGITAL\IOMOD.PCX /C
RUN SLIDE C:\DIGITAL\VALUE.PCX /C
GOTO LB38
ENDIF    /* GRAPHICS LOOP
ENDIF    /* CURRENT PROBLEM
/*
IF [THC PROBLEM] = "EMPTY ZERO GAS CYLINDER"
ASK [THC_ZGAS]
ENDIF    /* CURRENT PROBLEM
/*
IF [THC PROBLEM] = "EMPTY SPAN GAS CYLINDER"
ASK [THC_SGAS]
ENDIF    /* CURRENT PROBLEM
/*
IF [THC PROBLEM] = "THC ANALYZER ZERO DRIFT"
ASK [THC_ZDR]
ENDIF    /* CURRENT PROBLEM
/*
IF [THC PROBLEM] = "THC ANALYZER SENSITIVITY CHANGE"
:LB39
ASK [THC_SDR]
IF [THC_SDR] = "G" OR [THC_SDR] = "g"
RUN SLIDE C:\DIGITAL\FLOW400.PCX /C
RUN SLIDE C:\DIGITAL\THCINT.PCX /C
GOTO LB39
ENDIF    /* GRAPHICS LOOP
ENDIF    /* CURRENT PROBLEM
```

```
/*
IF [THC PROBLEM] = "FUEL/AIR MIX OUTSIDE OPTIMAL RATIO"
:LB40
ASK [THC_OMIX]
IF [THC_OMIX] = "G" OR [THC_OMIX] = "g"
RUN SLIDE C:\DIGITAL\FLOW400.PCX /C
RUN SLIDE C:\DIGITAL\THCINT.PCX /C
GOTO LB40
ENDIF    /* GRAPHICS LOOP
ENDIF    /* CURRENT PROBLEM
/*
IF [THC PROBLEM] = "THC INTERNAL SAMPLE PRESSURE LOW"
:LB41
ASK [THC_ISP]
IF [THC_ISP] = "G" OR [THC_ISP] = "g"
RUN SLIDE C:\DIGITAL\FLOW400.PCX /C
RUN SLIDE C:\DIGITAL\THCINT.PCX /C
GOTO LB41
ENDIF    /* GRAPHICS LOOP
ENDIF    /* CURRENT PROBLEM
/*
( REMEDIAL ACTION FILES FOR SEVERAL ANALYZERS NOT SHOWN )
/*
RUN DATIME / D /* GET DATE AND TIME FOR REPORT HEADER TIMESTAMP
REPORT SANFAVAT.OUT   /* LOG CURRENT PROBLEMS TO DISK
:REPLOOP
/*
/* CLEAR QUALIFIERS, VARIABLES, AND RULES FOR NEXT PASS THROUGH
EXPERT SYSTEM
/*
CLEAR Q ALL
CLEAR V ALL
CLEAR R ALL
/*
/* SET INITIAL VALUES FOR SOME VARIABLES (MUST BE THE SAME AS
DATALIST)
/*
SET [GLOBAL PROBLEM] "NONE"
SET [PURIFIER PROBLEM] "NONE"
SET [4N2 O2 PROBLEM] "NONE"
SET [3N2 O2 PROBLEM] "NONE"
SET [H2O PROBLEM] "NONE"
SET [THC PROBLEM] "NONE"
SET [RGA PROBLEM] "NONE"
SET [CO2 PROBLEM] "NONE"
SET [4N2 CNC PROBLEM] "NONE"
SET [4N2 ULPC PROBLEM] "NONE"
SET [3N2 CNC PROBLEM] "NONE"
SET [3N2 ULPC PROBLEM] "NONE"
SET [CO2 SP MIN] 11.0
SET [CO2 SP MAX] 13.0
SET [CO2 RP MIN] 11.0
SET [CO2 RP MAX] 13.0
/*
/* END OF OPERATOR ASSISTED PASS THROUGH RULE BASE
/*
GOTO START
/*
:FINISH
EXIT
```

Figure 4A:
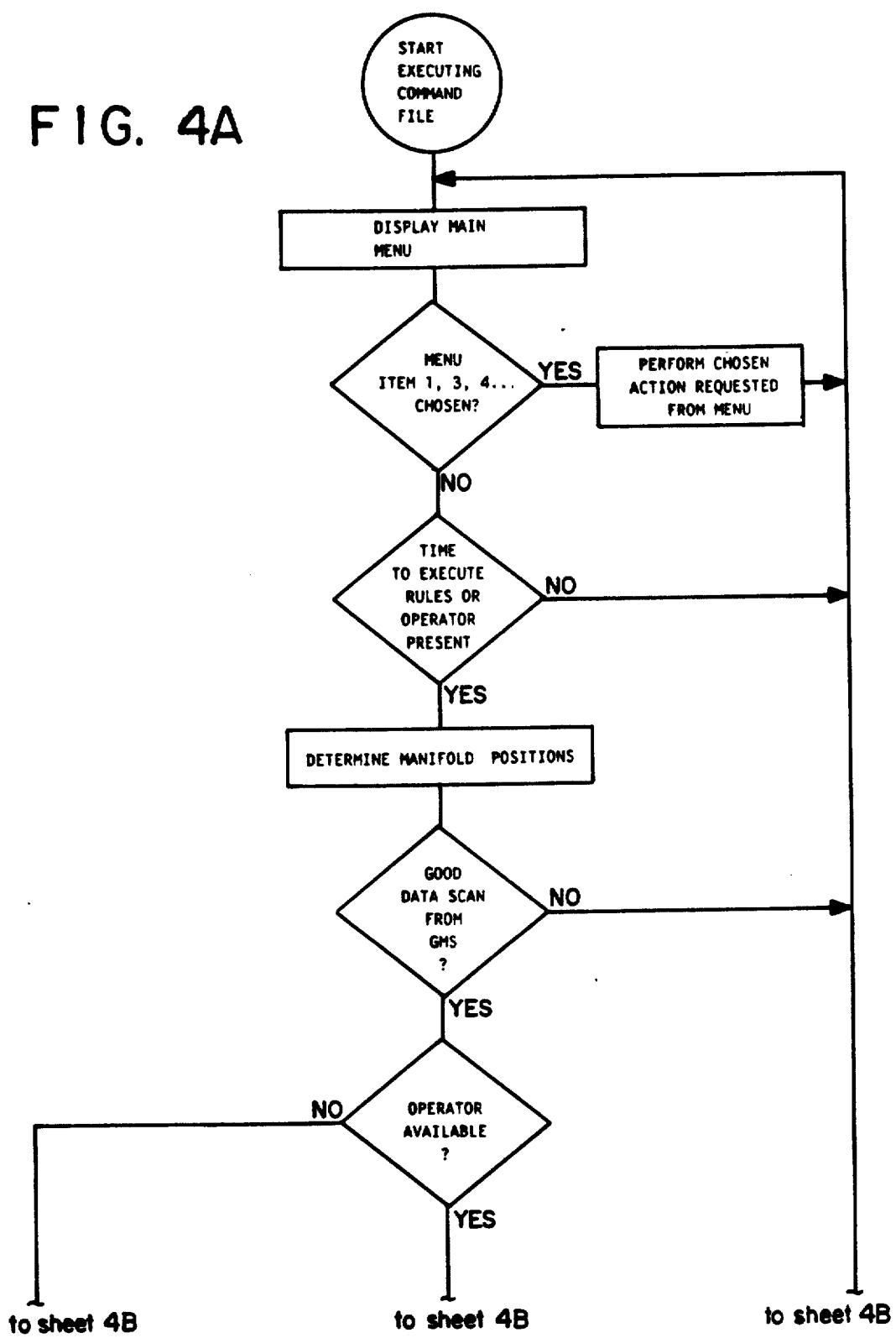
FIGS. 4A and 4B represent a logic flow chart of the command program for directing the expert system shell of FIG. 1.
Figure 4B:
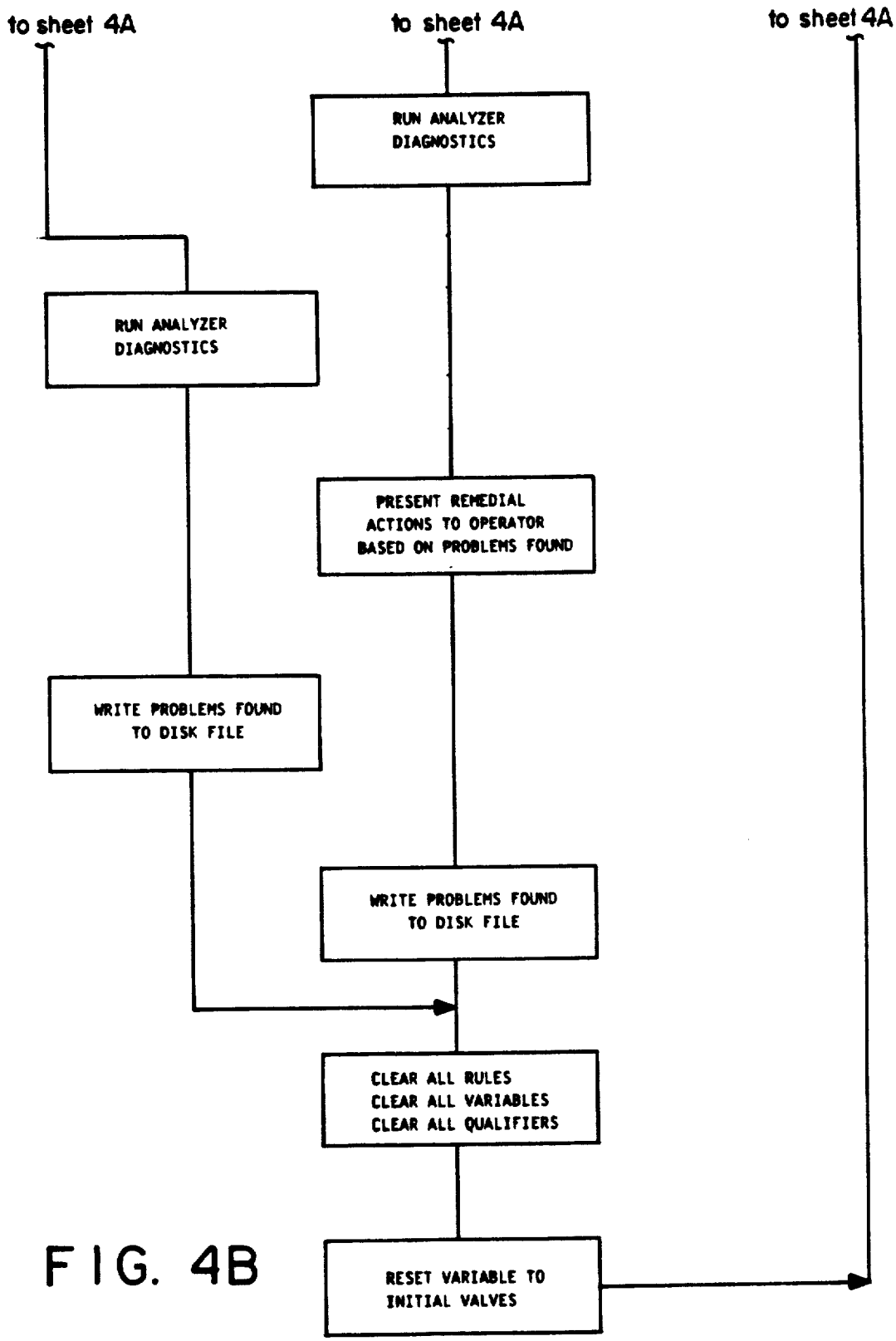

As apparent from the logic flow chart of FIGS. 4A and 4B the command file is executed automatically at preselected time intervals for automatically executing the shell unless the previously scanned data was improperly read. If the scanned data is invalid the execution of the shell is aborted until scan data from the one board computer 25 is read as valid or unless a particular action is chosen by an operator from the main menu of the PC. If the data scan is valid then the analyzer diagnostic is run whether an operator is present or not. The distinction resides in the provision for remedial action which occurs only in the presence of an operator. The initial command as indicated by the command rule statements is to run the program identified as VPOS to determine which of the manifold valves controlling the flow of either the sample, zero or span gas is activated based on the computer data values of S1917D, S1917E and S1917E assigned to identify flow valve positions. The command program, after determining the presence of an operator proceeds to provide remedial action based upon the existence of a global problem such as a gauge failure, power supply failure or low pressure respectively. The existence of a global problem is determined in a logical hierarchy with each global problem evaluated following a linear succession of priority to determine its existence and, if so, to match the problem with a remedial action in the remedial action file. A remedial action exists for each problem. A remedial action screen provides a graphical presentation of the identified problem with the corresponding remedial action. The remedial action is represented as data to which a variable value has been assigned in the PC computer. The display of the remedial action will provide the operator with a direction for solving the problem or an in-depth analysis of how to solve the problem. For example, if the problem is identified as a problem in the total hydrocarbon analyzer based on the fuel pressure being out of range then the command file will provide access to the screen file to provide an appropriate block of remedial text corresponding to the specifically identified problem. In addition the command file directs the shell to write all of the problems assigned by the rule base program to a computer disk file for printing. All previous information is then cleared and initialized with all problems to "NONE" for a subsequent run. When an operator is not present no remedial action is provided. Instead all of the uncovered problems are sent to the computer disk file and printed.

What is claimed is:

1. A process for the continuous analysis of trace contaminates in a process gas selected from the group consisting of $O_2$, N, Ar and $H_2$ and for identifying, storing and recording data representative of such trace contaminants in said process gas, for analyzing the stored data to identify erroneous analysis data and for identifying remedial actions to remedy the conditions causing said erroneous analysis comprising the steps of:

sampling said process gas to provide a stream of sample gas;

passing said stream of sample gas through a plurality of analyzers to determine the presence of one or more trace contaminants selected from the group consisting of $O_2$, $H_2$, CO, $CO_2$, hydrocarbons water moisture ($H_2O$) and particulate matter, with such selection being distinct from the selection of said process gas;

generating an output signal from each analyzer corresponding to the level of impurity for each trace contaminant under investigation;

generating a status signal representative of preselected parameters of analyzer operation corresponding to the operating status of one or more of said analyzers;

transferring said status signals and said output signals to a computer for storage in the form of data values;

analyzing said data values for the existence of a problem using an expert system rule base program consisting of a multiplicity of rules arranged to form statements corresponding to different problems;

executing said rule base program using an expert system shell with each problem recognized when said data values fall outside defined limits or are not present;

storing a file of remedial actions for a preselected number of problem conditions;

directing said expert system shell to select the examination of said rules in said rule base program in a predetermined hierarchy and in a linear sequence and matching problems identified by execution of said rule base program with one or more preselected remedial actions in said remedial action file.

2. A process as defined in claim 1 wherein each identified problem and the corresponding remedial action is displayed on a display monitor in the presence of an operator.

3. A process as defined in claim 2 wherein each output signal from said analyzer corresponds to analytical data in analog or digital form representative of the level of the trace contaminant under examination.

4. A process as defined in claim 3 wherein the analog data is converted to a digital signal for storage in said computer.

5. A process as defined in claim 3 wherein a status signal is generated representative of at least the following parameters: gas sample pressure to each analyzer, analyzer operating range, temperature, flow conditions and valve positions.

6. A process as defined in claim 1 wherein said process analyzers comprise an oxygen analyzer, a water moisture analyzer, a hydrogen and carbon monoxide analyzer, a total hydrocarbon analyzer and particle analyzers.

7. A process as defined in claim 6 wherein said particle analyzers include a standard laser particle counter and a condensation nucleus counter.

8. A process as defined in claim 6 wherein said rule based program, is executed in a linear forward no backward sequence.

9. A process as defined in claim 8 wherein said rule based program is an interactive program which requests identification of an operator and provides for a dialog with such operator to receive additional status input information as identified by said rule based program.

10. A process as defined in claim 9 wherein when an operator is not acknowledged as present all identified problems are assigned to a computer disk file for printing.

* * * * *